(12) United States Patent
Pernot et al.

(10) Patent No.: US 9,757,335 B2
(45) Date of Patent: Sep. 12, 2017

(54) METHOD FOR INCORPORATING ACTIVE AGENTS INTO A HYDROPHILIC POLYMER FOAM

(71) Applicant: LABORATOIRES URGO, Chenove (FR)

(72) Inventors: Jean-Marc Henri Maurice Pernot, Dijon (FR); Anne-Laure Ravenet, Chalon-sur-Saone (FR)

(73) Assignee: LABORATOIRES URGO, Chenove (FR)

(*) Notice: Subject to any disclaimer, the term of this patent is extended or adjusted under 35 U.S.C. 154(b) by 0 days.

(21) Appl. No.: 14/653,217

(22) PCT Filed: Dec. 17, 2013

(86) PCT No.: PCT/FR2013/053111
§ 371 (c)(1),
(2) Date: Jun. 17, 2015

(87) PCT Pub. No.: WO2014/096668
PCT Pub. Date: Jun. 26, 2014

(65) Prior Publication Data
US 2015/0328154 A1 Nov. 19, 2015

(30) Foreign Application Priority Data

Dec. 18, 2012 (FR) .................................. 12 62195

(51) Int. Cl.
| | | |
|---|---|---|
| *A61K 9/12* | (2006.01) |
| *A61K 8/04* | (2006.01) |
| *A61K 8/87* | (2006.01) |
| *A61K 47/34* | (2017.01) |
| *A61K 31/17* | (2006.01) |
| *A61K 31/7016* | (2006.01) |
| *A61F 13/00* | (2006.01) |
| *A61L 15/44* | (2006.01) |
| *B29C 44/12* | (2006.01) |
| *C08J 9/28* | (2006.01) |

(52) U.S. Cl.
CPC ........ *A61K 9/122* (2013.01); *A61F 13/00991* (2013.01); *A61K 8/046* (2013.01); *A61K 8/87* (2013.01); *A61K 31/17* (2013.01); *A61K 31/7016* (2013.01); *A61K 47/34* (2013.01); *A61L 15/44* (2013.01); *B29C 44/12* (2013.01); *C08J 9/28* (2013.01); *A61K 2800/10* (2013.01); *A61K 2800/56* (2013.01); *C08J 2201/0504* (2013.01); *C08J 2207/10* (2013.01); *C08J 2375/04* (2013.01)

(58) Field of Classification Search
CPC ............. C08G 18/10; A61F 13/00991; A61K 2800/56; C08J 2207/10; C08J 2207/12
See application file for complete search history.

(56) References Cited

U.S. PATENT DOCUMENTS

| | | | |
|---|---|---|---|
| 4,233,969 A * | 11/1980 | Lock ................. | A61F 13/00017 521/51 |
| 5,098,621 A | 3/1992 | Hermann | |
| 2009/0069736 A1* | 3/2009 | Park .................... | A61L 26/0019 602/46 |

FOREIGN PATENT DOCUMENTS

WO 2008157711 12/2008

OTHER PUBLICATIONS

International Search Report, Mar. 25, 2014; PCT/FR2013/053111.

* cited by examiner

*Primary Examiner* — Melissa Rioja
(74) *Attorney, Agent, or Firm* — Hamre, Schumann, Mueller & Larson, P.C.

(57) ABSTRACT

The present invention consists of a novel process for the incorporation of one or more water-soluble active agents in a hydrophilic polymer foam. Said process makes it possible in particular to obtain a hydrophilic polyurethane foam exhibiting a gradient of active agents. This process is of particular use when manufacturing hydrophilic polyurethane foams intended for medical, cosmetic and dermocosmetic purposes.

12 Claims, No Drawings

METHOD FOR INCORPORATING ACTIVE AGENTS INTO A HYDROPHILIC POLYMER FOAM

The present invention consists of a novel process for the incorporation of one or more water-soluble active agents in a hydrophilic polymer foam. Said process makes it possible in particular to obtain a hydrophilic polyurethane foam exhibiting a gradient of active agents. This process is of particular use when manufacturing especially hydrophilic polyurethane foams intended for medical, cosmetic and dermocosmetic purposes.

PRIOR STATE OF THE ART

The majority of conventional polymer foams are characterized by their hydrophobicity.

However, some treatments require the use of foams which absorb exudates; thus, hydrophilic polymer foams have been developed for these uses. Polymer foams include polyurethane foams and polyvinyl alcohol (PVA) foams. Hydrophilic polyurethane foams are generally prepared from a process in which a hydrophilic prepolymer having isocyanate end groups is mixed and reacted with water.

In medical, cosmetic and dermocosmetic fields, a number of manufacturers of hydrophilic polymer foams have in the past provided for the incorporation therein of advantageous active principles effective in particular in the healing of wounds.

Essentially two methods of incorporation of active principles in hydrophilic polymer foams are singled out.

A first method consists of the impregnation of a foam by immersion of the latter in a solution of active agent, this stage being followed, in a second step, by a stage of drying and of evaporation of the solvent. This type of process nevertheless has a serious disadvantage: the fact of exposing this product to relatively high drying temperatures and for relatively prolonged period of time can reduce the activity of the active principle.

The second method of incorporation of an active principle within a hydrophilic polymer foam which is particularly used consists in mixing the active principle with the precursor reactants of the foam. A problem common to both these processes for the incorporation of active principles in a hydrophilic polymer foam is the metering of the active agent to be introduced. The reliability of the metering becomes more sensitive as the dosage becomes smaller. Thus, losses of compounds may be observed. The majority of these active principles are very particularly expensive and good management of their metering during their incorporation in the final product is thus essential.

The patent application U.S. Pat. No. 5,098,621 of Twin Rivers has described a process for spraying a layer of micropackaged water-insoluble active principle over the internal surface of the tank of an applicator. An aqueous phase comprising water, prepolymer and surfactant is subsequently poured over the support. This document provides an applicator device for active principles which prevents the premature release of the active principle by bonding the latter to the foam. The active principle trapped at the surface of the foam is released solely under the action of a mechanical stress. This is because, during the stage of polymerization of the foam, the hydrophobic micropackaged active agents remain intact and are thus found attached to the surface of the foam, guaranteeing their integrity, thus allowing them to be released solely after exerting a mechanical stress.

The patent application WO 2006/007844 of Coloplast has proposed to carry out a process for the addition of active principles within an absorbent dressing which solves the problems underlined above. The preparation method described comprises spraying the active principle over the central portion of the surface of the absorbent component. The active principle is preferably found on the surface or in the upper parts of the thickness of the absorbent component. For example, 90% of the active principle is found in the upper quarter of the thickness of the absorbent component. The spraying of said active principle is carried out by means of an LVLP spraying device (device which dispenses low volumes of products under low pressures). The absorbent layer of this device can be prepared from materials formed from the list of the foams, alginates, polysaccharides, chitosans, super-absorbents or a mixture of these. There are many disadvantages to this manufacturing process: it is carried out in several stages and incorporation by spraying of the active agent within the absorbent device is carried out in a stage subsequent to that of the manufacture of said device.

It thus appears necessary to produce a process which is more advantageous economically and which does not require an additional treatment stage subsequent to the preparation of the device itself, while guaranteeing accurate metering of the active principle and a gradient of active principle in the thickness of the foam.

The applicant company has developed a novel process which responds to these problem, a process for the incorporation of one or more water-soluble active agents in a hydrophilic polymer foam comprising the stages of deposition of the water-soluble active agent or agents on an impermeable nonporous support, preparation of a prepolymer mixture in aqueous solution, pouring said mixture obtained over said support, polymerization and production of a hydrophilic polymer foam incorporating one or more water-soluble active principles, and finally drying the hydrophilic polymer foam.

SUMMARY OF THE INVENTION

Thus, the present invention consists of a novel process for the incorporation of at least one cosmetic or pharmaceutical water-soluble active agent in a hydrophilic polymer foam, comprising the stages of:
a) deposition of the water-soluble active agent on an impermeable nonporous support,
b) preparation of a precursor mixture of the foam in the form of an aqueous dispersion comprising either monomers or prepolymers,
c) pouring the mixture obtained in stage b) over the active agent which has been deposited on the support at the end of stage a),
d) polymerization and production of the hydrophilic polymer foam incorporating the water-soluble active agent,
e) drying the hydrophilic polymer foam.

The water-soluble active agent can be chosen from the list consisting of antibacterial agents, antiinflammatories, keratolytic agents, immunomodulating agents, chelating agents, pH-modifying agents, compounds of the extracellular matrix, agents which promote healing, antiviral agents, antifungal agents and painkillers.

The water-soluble active agent is preferably urea, hyaluronic acid or a synthetic polysulfated oligosaccharide having from 1 to 4 monosaccharide units, its salts or its complexes.

The water-soluble active agent can be deposited alone in the pure form or in solution. It can also have been incorporated, prior to deposition, in a water-soluble matrix.

The impermeable nonporous support can, for example, be a silicone-treated polyethylene-coated paper or a silicone-treated polyester film.

The prepolymer is in particular a prepolymer of poly(alkyleneoxy)polyol type.

A surfactant, in particular a surfactant of cationic or anionic or nonionic type or a silicone-based surfactant, can be added to it.

DETAILED DESCRIPTION OF THE INVENTION

Other characteristics and advantages of the invention will become more clearly apparent on reading the description which follows of two preferred embodiments of the invention, given by way of example.

Thus, the present invention consists of a novel process for the incorporation of at least one cosmetic or pharmaceutical water-soluble active agent in a hydrophilic polymer foam, comprising the stages of:
a) deposition of the water-soluble active agent on an impermeable nonporous support,
b) preparation of a precursor mixture of the foam in the form of an aqueous dispersion comprising either monomers or prepolymers,
c) pouring the mixture obtained in stage b) over the active agent which has been deposited on the support at the end of stage a),
d) polymerization and production of the hydrophilic polymer foam incorporating the water-soluble active agent,
e) drying the hydrophilic polymer foam.

Prior to stage a), it is possible to prepare an aqueous solution or dispersion of the water-soluble active agent which is subsequently deposited on the support, during stage a) for example by spraying.

The polymer foam can be chosen from polyurethane foams and polyvinyl alcohol (PVA) foams.

According to a preferred embodiment of the invention, the polymer foam is a hydrophilic polyurethane foam.

The prepolymer of the hydrophilic polyurethane foam may be already synthesized.

On the other hand, if the prepolymer has to be prepared, it is possible to produce a hydrophilic polyurethane foam in one or two stages. In one stage, the hydrophilic polyurethane foam is produced by reacting the polyols, the polyisocyanates, the water and a surfactant simultaneously. In two stages, the prepolymer is synthesized in a stage prior to the addition of water and a surfactant, by reacting the polyols and the polyisocyanates.

If the prepolymer is already synthesized, it is sufficient simply to react the latter with water and a surfactant in order to obtain a hydrophilic polyurethane foam. It should be noted that the surfactant does not constitute an essential compound with regard to the preparation of a hydrophilic polyurethane foam; it is only optional but plays a major role with regard to the control of the reaction and with regard to the physicochemical characteristics of the foam obtained.

"Polyol" is understood to mean, within the meaning of the present invention, any natural or synthetic compound exhibiting several hydroxyl groups, said groups being capable of reacting with isocyanate groups to result in urethane bridges. In the case of polyols of synthetic origin, polyethylene glycol and polyethers are the most frequently used by manufacturers of hydrophilic polyurethane foams, in particular due to their hydrophilicity. In the case of polyols of natural origin, the latter can be derived from the products defined by the following nonlimiting list: xylose, arabinose, glucose, sucrose, dextrins, glycerol, starch, castor oil, soybean oil or vegetable oil. In the context of the present invention, the polyols preferably used will be of the poly(ethyleneoxy)polyol or poly(propyleneoxy)polyol type or a mixture of the two.

"Polyisocyanates" is understood to mean any compound which can be chosen from the group consisting of toluene 2,4-diisocyanate, toluene 2,6-diisocyanate, ethylidene diisocyanate, propylene 1,2-diisocyanate, cyclohexylene 1,2-diisocyanate, cyclohexylene 1,4-diisocyanate, triphenylmethane 4,4',4''-triisocyanate, m-phenylene diisocyanate, 4,4'-biphenylene diisocyanate, 3,3'-dichloro-4,4'-biphenylene diisocyanate, benzene 1,3,5-triisocyanate, toluene 2,4,6-triisocyanate, diphenyl 2,4,4'-triisocyanate, 1,4-tetramethylene diisocyanate, 1,6-hexamethylene diisocyanate, 1,10-decamethylene diisocyanate, xylene diisocyanate, chlorophenylene diisocyanate, diphenylmethane 4,4'-diisocyanate, naphthalene 1,5-diisocyanate, cumene 2,4-diisocyanate, 4-methoxy-1,3-phenylene diisocyanate, 4-chloro-1,3-phenylene diisocyanate, 4-bromo-1,3-phenylene diisocyanate, 4-ethoxy-1,3-phenylene diisocyanate, 4-bromo-1,3-phenylene diisocyanate, 4-ethoxy-1,3-phenylene diisocyanate, 2,4-diisocyanatodiphenyl ether, 5,6-dimethyl-1,3-phenylene diisocyanate, 2,4-dimethyl-1,3-phenylene diisocyanate, 4,4'-diisocyanatodiphenyl ether, benzidine diisocyanate, xylene $\alpha,\alpha$-diisothiocyanate, 3,3'-dimethyl-4,4'-biphenylene diisocyanate, 2,2',5,5'-tetramethyl-4,4'-biphenylene diisocyanate, 4,4'-methylene-bis(phenyl isocyanate), 4,4'-sulfonylbis(phenyl isocyanate), 4,4'-methylenedi(o-tolyl isocyanate), ethylene diisocyanate, ethylene diisothiocyanate and trimethyl-ene diisocyanate.

The foam can be a hydrophilic polyurethane foam which is obtained with a precursor mixture comprising a prepolymer of poly(alkyleneoxy)polyol type.

The constituent prepolymers of a hydrophilic polyurethane foam are preferably of poly(alkyleneoxy)polyol type. Among these prepolymers, polyurethane prepolymers comprising isocyanate end bonds are particularly preferred, such as, for example, the prepolymers sold under the Hypol® brand by Dow, the Prepol® brand by Lendell Manufacturing Inc., the Hydropol® brand by Mace Adhesives & Coatings Co., the Aquapol® brand by Carpenter Co. and the Urepol® brand by EnviroChem Technologies. These isocyanate end bonds can correspond to aromatic isocyanates, such as, for example, toluenediisocyanate (TDI) or methylenediphenyl isocyanate (MDI), or also aliphatic isocyanate groups, such as, for example, isopborone diisocyanate (IPDI) but also hydrogenated methylenediphenyl isocyanate (HMDI). The products of the Hypol® brand which can be used in the context of the present invention include Hypol 2000®, Hypol 2002 E®, Hypol 3000®, Hypol 4000® or Hypol 5000®. Preferably, in the context of the present invention, the prepolymer used in the preparation of the hydrophilic polyurethane foam will be Hypol 2002 E®.

The precursor mixture of the foam can comprise a surfactant of cationic, anionic or nonionic type or a silicone-based surfactant.

According to one embodiment, the precursor mixture of the foam comprises a nonionic surfactant.

A wide variety of surfactants known in the state of the art can be provided with regard to its incorporation in the preparation of a hydrophilic polyurethane foam. Among known surfactants, cationic surfactants, nonionic surfactants or also anionic surfactants, such as salts of fatty acids, salts of esters of sulfuric acids, salts of esters of phosphoric acids and sulfonates, can be present in the base composition which is a subject matter of the present invention. Preferably, the surfactants used in the context of the preparation of a hydrophilic polyurethane foam will be surfactants of nonionic type, such as some products sold by BASF under the Pluronic® name. More preferably still, the surfactant used in the preparation of a hydrophilic polyurethane foam is Pluronic PE6200®, which is a copolymer of ethylene oxide and of propylene oxide, or also Pluronic PE6800®. Another known type of surfactant which can be used in the context of the present invention is represented by silicone-based surfactants. Mention may be made, among these, of hydrolyzable polysiloxane/polyoxyalkylene copolymers, nonhydrolyzable polysiloxane/polyoxyalkylene copolymers, cyanoalkylpolysiloxanes, alkylpoly-siloxanes, polydimethylsiloxanes and polyoxyalkylene-modified dimethylpolysiloxanes. The type of silicone-based surfactant used and the amount necessary depend on the type of foam to be produced.

The process which is a subject matter of the present invention consists in incorporating one or more water-soluble active agents within a conventional hydrophilic polyurethane foam. This incorporation was carried out by deposition of the water-soluble active agent or agents on a nonporous and impermeable support, the deposition prior to the pouring of the precursor reaction mixture of the foam.

"Impermeable nonporous support" is understood to mean any support intended to be coated with the reaction mixture giving rise to the hydrophilic polyurethane foam. Preferably, this support is silicone-treated in order to prevent the newly formed foam from adhering to the support. Use may be made, as impermeable nonporous support, by way of examples, of a silicone-treated polyethylene-coated paper or a silicone-treated polyester film.

The support is preferably separated from the foam after the latter has been dried as it is used essentially as pouring surface during the manufacture of the foam and is not of use during the use of the foam, in particular for absorbing exudates from a wound.

Consequently, according to a specific embodiment, the process of the invention comprises a stage f) during which the support is separated from the foam after the latter has been dried in stage e).

"Water-soluble active agent" is understood to mean, within the meaning of the present invention, any compound which is provided in the form of water-soluble particles. Thus, particles of a water-soluble active agent which are coated with a hydrophobic material do not constitute a water-soluble active agent within the meaning of the invention. This is because preference is given, in the context of the present invention, to use of a water-soluble active principle which dissolves or disperses significantly in the aqueous dispersion comprising the precursor mixture of the foam, during the pouring thereof on the support.

The water-soluble active agent is chosen from the list consisting of antibacterial agents, anti-inflammatory agents, keratolytic agents, immunomodulating agents, chelating agents, pH-modifying agents, compounds of the extracellular matrix, agents which promote healing, antiviral agents, antifungal agents and painkillers.

"Agent which promotes healing" is understood to mean, within the meaning of the present invention, any compound chosen from the nonlimiting list consisting of retinol, vitamin A, vitamin E and its derivatives, N-acetylhydroxyproline, *Centella asiatica* extracts, papaine, hyaluronic acid, synthetic polysulfated oligosaccharides having from 1 to 4 monosaccharide units, their salts and their complexes, such as, for example, alkali metal salts of sucrose octasulfate (these include, inter alia, the potassium salt of sucrose octasulfate or the sodium salt of sucrose octasulfate), sucralfate, amine acid salts of sucrose octasulfate or the silver salt of sucrose octasulfate, allantoin and metformin.

"Antiviral agent" is understood to mean, within the meaning of the present invention, any compound chosen from the nonlimiting list consisting of aciclovir, famciclovir and ritonavir.

"Antifungal agent" is understood to mean, within the meaning of the present invention, any compound chosen from the nonlimiting list consisting of nystatin, amphotericin B, natamycin, miconazole, ketoconazole, clotrimazole, econazole, bifonazole, butoconazole, fenticonazole, isoconazole, oxiconazole, sertaconazole, sulconazole, thiabendazole, tioconazole, fluconazole, itraconazole, ravuconazole, posaconazole, voriconazole, allylamine, terbinafine, amorolfine, naftifine and butenafine.

"Painkiller" is understood to mean, within the meaning of the present invention, any compound chosen from the nonlimiting list consisting of paracetamol, codeine, dextropropoxyphene, tramadol, morphine and its derivatives, and corticoids and their derivatives.

"Antibacterial agent" is understood to mean, within the meaning of the present invention, any compound chosen from the nonlimiting list consisting of silver salts or complexes (such as silver sulfates, silver nitrates, silver sulfamides or silver-based zeolites), zinc or copper salts, metronidazole, neomycin, penicillins, clavulanic acid, tetracyclins, minocycline, chlortetracycline, aminoglycosides, amikacin, gentamicin or probiotics.

"Anti-inflammatory agent" is understood to mean, within the meaning of the present invention, any compound chosen from the nonlimiting list consisting of nonsteroidal antiinflammatories (NSAI), aspirin or acetylsalicylic acid, ibuprofen, ketoprofen, flurbiprofen, diclofenac, aceclofenac, ketorolac, meloxicam, piroxicam, tenoxicam, naproxen, indomethacin, naproxcinod, nimesulide, celecoxib, etoricoxib, parecoxib, rofecoxib, valdecoxib, phenylbutazone, niflumic acid and mefenamic acid.

"Keratolytic agent" is understood to mean, within the meaning of the present invention, any compound chosen from the nonlimiting list consisting of salicylic acid, zinc salicylate, ascorbic acid, α-hydroxylated acids (such as glycolic acid, lactic acid, malic acid, citric acid or tartaric acid), silver maple, sour cherry or tamarind extracts, urea, Keratoline (sold by Sederma) and papaine.

Finally, "immunomodulating agent" is understood to mean β-glucan, "chelating agent" is understood to mean ethylenediaminetetraacetic acid (EDTA) and hydroxamic acids, "pH-modifying agent" is understood to mean sodium bicarbonate and "agent of the extracellular matrix" is understood to mean glycosaminoglycans, hyaluronic acid, dermatan sulfate, heparan sulfate, elastins and laminin.

Preferably, the active agents of the invention are urea (sold by Fisher Scientific), hyaluronic acid (sold by Soliance® under the Renovhyal® trade name) or a synthetic polysulfated oligosaccharide having from 1 to 4 monosaccharide units, its salts and its complexes, such as, for example, alkali metal salts of sucrose octasulfate (these include, inter alia, the potassium salt of sucrose octasulfate or the sodium salt of sucrose octasulfate), sucralfate, amine acid salts of sucrose octasulfate or the silver salt of sucrose octasulfate.

Said active agents can be incorporated in the foam in amounts of between 0.01% and 40% of the final weight of the hydrophilic polyurethane foam obtained and preferably between 0.1% and 20% of the final weight of the hydrophilic polyurethane foam obtained.

These active agents are deposited on the impermeable nonporous support in the aqueous dispersion, solution or powder form. According to another embodiment of the invention, they may have been incorporated beforehand in a water-soluble matrix.

When the active agents are deposited on the nonporous and impermeable support, it is possible to deposit them either by dusting over the surface of the support or to carry out a simple spraying of a water/active agent mixture over the surface of the support in question. In the latter case, the choice is or is not made to dry this combination thus obtained, for example by passing under an oven.

The active agents can be incorporated in a water-soluble matrix before being deposited on the support. Consequently, prior to stage a), it is possible to prepare a water-soluble matrix comprising the water-soluble active agent, which matrix is subsequently deposited on the support during stage a).

"Water-soluble matrix" is understood to mean, whatever the type of matrix, any material capable of dissolving in water under a slight mechanical pumping to give a homogeneous solution, within a time interval of less than 10 seconds and preferably of less than 2 seconds, starting from when said material is brought into contact with said water.

The water-soluble matrix acts as support for the active agent during the pouring of the reaction mixture which makes it possible to obtain the foam. This matrix disappears as soon as it comes into contact with the constituent reaction mixture of the hydrophilic polyurethane foam or rather diffuses into the whole of this reaction mixture, thus releasing the water-soluble active agents, which active agents consequently establish a gradient within the foam formed. The active agents are thus released into the foam and diffuse into the foam along a concentration gradient perpendicular to the surface of the support.

In the process of the invention, the polymer foam is hydrophilic. A hydrophobic matrix is targeted at keeping the active agent within it in order for it to be released after the pouring of the constituent reaction mixture of the foam. In contrast, the water-soluble matrix used in the context of the invention makes it possible to dissolve the active agent at the time of the polymerization of the foam. The use of a hydrophobic matrix is thus prohibited, whatever the envisaged embodiment of the present invention.

"Gradient of active agent" is understood to mean any active agent preferably present in the lower layers of the foam, the layers closest to the support. Preferably, 80% of the total weight of the active agent introduced in the process for the manufacture of the foam is found in the lower 33% of the foam and, more preferably still, 90% of the total weight of the active agent introduced in the process for the manufacture of the foam is found in the lower 33% of the foam.

The advantage of having available such a gradient of active agent is the offer of a better availability of the active agent at the surface of the wound or of the skin of the individual.

The values for gradient of active agents within a hydrophilic polyurethane foam are determined via a conventional method for measuring the release of the active agent or agents present in each slice of foam tested. The values for active agent release thus obtained are proportional to the amounts of active agent present in each slice of foam tested and make it possible to obtain the value for gradient of active agent in the foam.

The active agents can be incorporated in a water-soluble matrix in the form either of agglomerates or of a net of nanofibers.

"Agglomerate" is understood to mean any aggregation of particles bonded to one another, said particles being composed, for at least 60% and preferably at least 80% among them, of a (or several) material(s) chosen from polysaccharides, proteins and synthetic polymers, and capable of dissolving in less than 10 seconds and preferably again in less than 2 seconds from being brought into contact with water. These agglomerates comprise water-soluble active agents as defined above. According to a specific embodiment of the invention, the agglomerates comprise an (or several) active agent(s). In the case where a plurality of active agents is used, these can be incorporated either individually in separate agglomerates or in the form of a mixture within one and the same agglomerate. An agglomerate can in particular denote an assembly of particles having small sizes, that is to say having a mean dimension of between 500 nm and 1000 µm, preferably of between 1 µm and 500 µm, which are bonded together, for example in raspberry form.

Each agglomerate generally has a mean dimension of between 5 and 2000 µm and will thus be composed of approximately 10 to 10000 particles, preferably of approximately 100 to 1000 particles.

Such agglomerates of particles can be prepared, in a way known per se, by wet granulation processes, such as, in particular, by spray drying or in a fluidized air bed, generally using water or an aqueous mixture as binder.

The amount of agglomerates deposited can vary within wide proportions and will generally be between 1 and 500 grams per square meter, preferably between 5 and 100 g/m$^2$.

Mention may be made, among the polysaccharides capable of being used in producing such agglomerates, of starch, modified starches, maltodextrin, gums, such as, in particular, gum arabic or acacia gum, cellulose, cellulose derivatives, such as, in particular, methylcellulose, carboxymethylcellulose, hydroxypropyl-cellulose or hydroxyethylcellulose, sugars, pectin and alginates.

Mention may be made, among the proteins capable of being used in producing such agglomerates, of gelatin, albumin and casein.

Mention may be made, among the synthetic polymers capable of being used in producing such agglomerates, of polyacrylates or polyvinyl alcohol.

"Net of nanofibers" is understood to mean any combination of nanofibers having a diameter of between 20 and 1000 nm and more preferably of between 50 and 500 nm preferably positioned according to a monolayer arrangement, forming a net analogous to a nonwoven, that is to say a random assemblage of nanofibers held in the form of a sheet by friction, cohesion or adhesion.

This net of nanofibers is composed, for at least 60% and preferably at least 80% among them, of a (or several) material(s) chosen from natural or synthetic polymers, and capable of dissolving in less than 10 seconds and preferably again in less than 2 seconds from being brought into contact with water.

The nets of nanofibers according to the invention can be obtained by aerodynamic drawing of molten polymers or of polymers in aqueous or solvent solution according to the technology known under the name of centrifugal spinning. The nets of nanofibers can also be obtained by the process known under the name of electrospinning.

Electrospinning is a technology which makes it possible to produce nanofibers by evaporation of a polymer solution or dispersion within a high-potential electric field. More specifically, this process consists in subjecting a sufficiently fluid solution or dispersion of a material, exiting from a very fine nozzle, to an electric potential of the order of 5 to 50 kV. Under the effect of this electric field, the drop exiting from the nozzle becomes electrically charged, assuming a substantially conical shape, and can be drawn into a jet to form a very fine fiber of nanometric to micrometric size when the electrical voltage is sufficiently high to break the surface tension of the drop. The fibers thus formed can be collected and stored in this state, for example on a collector, or alternatively be randomly deposited on a support in order to form a net similar to a nonwoven. This technology is particularly suitable for the preparation of microfibers or nanofibers based on polyvinyl alcohol.

Mention may be made, among the materials capable of being used according to the invention, of polyvinyl alcohol (PVA), polyvinylpyrrolidone (PVP), poly-ethyleneimine (PEI), polyethylene oxides (PEO), carboxymethylcellulose, alginates and the mixtures of these compounds.

In the case where the net of nanofibers is prepared by electrospinning, the active agents can be incorporated in the solution or dispersion subjected to the electrical field, thus making it possible to directly incorporate these active agents in the net of nanofibers. Said active agents can also optionally be deposited on the receptacle of the nanofibers.

The amount of nanofibers deposited can vary within wide proportions and will generally be between 0.5 and 200 g, and preferably between 1 and 30 g per square meter of adhesive mass.

EXAMPLES

Example 1: Preparation of a Hydrophilic Polyurethane Foam Incorporating Potassium Sucrose Octasulfate A silicone-treated polyethylene-coated paper, on which has been sprayed a 5% solution of potassium sucrose octasulfate, is laid down at the bottom of a disposable beaker.

In a second stage, 2 grams of Pluronic PE6200® are added, in a second beaker, to a solution of distilled water with a weight of 98 grams. This solution is homogenized using a propeller mixer at 500 revolutions/min.

In a third stage, 20 grams of Hypol 2002® are added to 40 grams of the final solution prepared in stage 2. This mixture is homogenized for a time of 20 seconds using a propeller mixer at 800 revolutions/min.

Finally, in a fourth and final stage, the reaction mixture obtained at the end of stage 3 is poured into the beaker containing the support on which has been sprayed beforehand the 5% solution of potassium sucrose octasulfate, corresponding to the support obtained at the end of stage 1. The foam is left to expand and then it is left to dry under an oven at 70° C. for at least 4 hours.

After separation of the foam obtained from the support, there is thus obtained a hydrophilic polyurethane foam incorporating potassium sucrose octasulfate.

Example 2: Preparation of a Hydrophilic Polyurethane Foam Incorporating Urea 2 grams of urea in the powder form are evenly distributed over silicone-treated polyethylene-coated paper at the bottom of a disposable beaker.

In a second stage, 2 grams of Pluronic PE6200® are added, in a second beaker, to a solution of distilled water with a weight of 98 grams. This solution is homogenized using a propeller mixer at 500 revolutions/min.

In a third stage, 20 grams of Hypol 2002® are added to 40 grams of the final solution prepared in stage 2. This mixture is homogenized for a time of 20 seconds using a propeller mixer at 800 revolutions/min.

Finally, in a fourth and final stage, the reaction mixture obtained at the end of stage 3 is poured onto the support on which is evenly distributed an amount of 2 grams of urea in the powder form, corresponding to the support obtained at the end of stage 1. The foam is left to expand and then it is left to dry under an oven at 70° C. for at least 4 hours.

After separation of the foam obtained from the support, there is thus obtained a hydrophilic polyurethane foam incorporating urea.

Example 3: Determination of the Values for Gradient of Active Agents of the Hydrophilic Polyurethane Foam Produced According to Example 1

The values for gradient of active agents, namely potassium sucrose octasulfate, within the hydrophilic polyurethane foam produced according to example 1 are determined via a method for measuring the release of the active agent or agents present in the foam, or the slice of foam in question.

The amount of active agent released is proportional to the amount of active agent present in the slice of foam in question.

In the present case, a slice of foam with a thickness of 3 mm and with an area of approximately 25 $cm^2$ is cut out from the lower third, median third and upper third of the newly formed foam. Each slice is representative of each foam third. Each slice is immersed in physiological saline at 37° C. for 24 hours. The physiological saline is recovered and assayed by HPLC. The release values are thus known.

The following are thus obtained:

| Test | Units | Samples analyzed | Mean release |
|---|---|---|---|
| Release of active agent present in the foam produced according to example 1 | % | Lower<br>Median<br>Upper | 99.8<br>0.1<br>0.1 |

The release of active agent from each slice is expressed as a function of the amount of active agent of the solution onto which the foam is poured.

Thus, virtually all of the amount of active agent (99.8%) is found in the bottom part of the foam, the part proximal to the skin of the individual.

Thus, 99.8% of the active agent is found in the lower third of the foam.

The invention claimed is:

1. A process for manufacturing a hydrophilic polymer foam exhibiting a gradient of a water-soluble active agent, the process comprising:
   a) deposition of the water-soluble active agent in the form of water-soluble particles on an impermeable nonporous support,
   b) preparation of a precursor mixture of the foam in the form of an aqueous dispersion comprising either monomers or prepolymers, c) pouring the mixture obtained in stage b) over the water-soluble particles that have been deposited on the support at the end of stage a), wherein said water-soluble particles dissolve in the aqueous dispersion comprising the precursor mixture of the foam, d) polymerization of the precursor mixture in which the water-soluble particles dissolved, and production of the hydrophilic polymer foam incorporating the water-soluble active agent, e) drying the hydrophilic polymer foam, and f) separating the impermeable nonporous support from the foam after the foam has been dried in stage e), wherein 80 to 90% of the total weight of the water-soluble active agent is found in the lower 33% of the total volume of the hydrophilic polymer foam, which is the volume of the foam closest to the impermeable nonporous support, at the end of stage e).

2. The process as claimed in claim 1, wherein the foam is a hydrophilic polyurethane foam which is obtained with a precursor mixture comprising a prepolymer of poly(alkyleneoxy) polyol type.

3. The process as claimed in claim 1, wherein the precursor mixture of the foam comprises a silicone-based surfactant.

4. The process as claimed in claim 1, wherein the precursor mixture of the foam comprises a nonionic surfactant.

5. The process as claimed in claim 1, wherein the water-soluble active agent is chosen from the group consisting of antibacterial agents, anti-inflammatory agents, keratolytic agents, immunomodulating agents, chelating agents, pH-modifying agents, compounds of the extracellular matrix, agents which promote healing, antiviral agents, antifungal agents and painkillers.

6. The process as claimed in claim 1, wherein the water-soluble active agent is urea or hyaluronic acid.

7. The process as claimed in claim 1, wherein the impermeable nonporous support is a silicone treated support.

8. The process as claimed in claim 1, wherein the water-soluble active agent is a synthetic polysulfated oligosaccharide having from 1 to 4 monosaccharide units, a salt of said polysulfated oligosaccharide, or a complex of said polysulfated oligosaccharide.

9. The process as claimed in claim 1, wherein 90% of the total weight of the water-soluble active agent introduced in the process for the manufacture of the hydrophilic polymer foam is found in the lower 33% of the hydrophilic polymer foam.

10. The process as claimed in claim 1, wherein the impermeable nonporous support is a silicone-treated polyethylene-coated paper or a silicone-treated polyester film.

11. The process as claimed in claim 1, wherein the water-soluble active agent in the form of water-soluble particles is deposited on the support by dusting.

12. The process as claimed in claim 1, where the water-soluble active agent in the form of water-soluble particles is deposited on the support in a water-soluble matrix, said water-soluble matrix diffusing into the precursor mixture after coming into contact with the precursor mixture in stage c) to allow the water-soluble active agent in the form of water-soluble particles to dissolve in the precursor mixture.

* * * * *